United States Patent [19]

Miyasaka et al.

[11] Patent Number: 4,873,181

[45] Date of Patent: Oct. 10, 1989

[54] SILVER HALIDE PHOTOGRAPHIC MATERIAL

[75] Inventors: Nobuaki Miyasaka; Shuzo Suga, both of Kanagawa, Japan

[73] Assignee: Fuji Photo Film Co., Ltd., Kanagawa, Japan

[21] Appl. No.: 206,922

[22] Filed: May 31, 1988

Related U.S. Application Data

[63] Continuation of Ser. No. 822,498, Jan. 27, 1986, abandoned.

[30] Foreign Application Priority Data

Jan. 25, 1985 [JP] Japan ................................. 60-11066

[51] Int. Cl.$^4$ ............................................... G03C 1/76
[52] U.S. Cl. .................................... 430/523; 430/611; 430/961
[58] Field of Search ..................... 430/523, 611, 961

[56] References Cited

U.S. PATENT DOCUMENTS 4,364,248  1/1983  Ranz et al. ......................... 430/523
4,400,462  8/1983  Ono et al. ......................... 430/523

FOREIGN PATENT DOCUMENTS 61-48832  3/1986  Japan .

Primary Examiner—Paul R. Michl
Assistant Examiner—Janet C. Baxter
Attorney, Agent, or Firm—Sughrue, Mion, Zinn, Macpeak & Seas

[57] ABSTRACT

A silver halide photographic material is described, comprising a support bearing at least one silver halide photographic emulsion layer and at least one auxiliary layer on one side or both sides thereof, wherein the silver halide photographic emulsion layer is a layer made of a light-sensitive silver halide emulsion containing silver iodide and an internally fogged silver halide emulsion, or is composed of a layer made of the light-sensitive silver halide emulsion containing silver iodide and a layer made of the internally fogged silver halide emulsion, and the auxiliary layer contains substantially non-light-sensitive silver halide grains having an average grain size of not more than 0.5 $\mu$m.

14 Claims, No Drawings

SILVER HALIDE PHOTOGRAPHIC MATERIAL

This is a continuation of application Ser. No. 822,498 filed 1/27/86, now abandoned.

FIELD OF THE INVENTION

The present invention relates to a silver halide photographic material (hereinafter also referred to more simply as a "light-sensitive material"). More particularly, it is concerned with a light-sensitive material providing developed silver of high covering power which is improved in development stability and graininess.

BACKGROUND OF THE INVENTION

The covering power of a silver halide emulsion is a matter of great concern for one engaged in preparation of silver halide emulsions. This is because if an emulsion having a high covering power is used, the amount of silver necessary to obtain a desired optical density can be decreased.

U.S. Pat. Nos. 2,996,382, 3,178,282, 3,397,987, and 3,607,278, British Pat. No. 1,426,277, etc., describe that the covering power of silver halide can be greatly increased by mixing a surface light-sensitive emulsion having a high silver iodide content and an internally fogged emulsion containing small grains.

It is also known that to increase the covering power of a silver halide emulsion, various additives can be added to the emulsion. The majority of additives capable of increasing the covering power are synthetic polymers or saccharides. Typical examples of such synthetic polymers are polyacrylamides such as those described in U.S. Pat. Nos. 3,271,158 and 3,514,289. Typical examples of such saccharides are dextran, as described in U.S. Pat. Nos. 3,063,838 and 3,272,631.

These additives, however, have a disadvantage in that if they are used in a sufficient amount to achieve the above object, the resulting light-sensitive material is excessively increased in contrast, because development activity is markedly increased, thereby resulting in a reduction of graininess.

Japanese Patent Application (OPI) No. 215647/83 (the term "OPI" as used herein refers to a published unexamined Japanese patent application) discloses a method for controlling gradation by separating surface light-sensitive layers and introducing internally fogged fine grains only in the low-sensitive layer. In accordance with this method, however, it is difficult to control the developing properties of areas composed of surface light-sensitive emulsion grains on the low-sensitive layer, and graininess of high density areas cannot be improved.

Moreover, since a high iodine content emulsion is used, if a light-sensitive material is continuously processed, iodine ions accumulate in the processing solution, and the amount of the iodine ion accumulated in the processing solution is significantly larger than that in the case of using the usual low iodine content light-sensitive material. Thus, if the number of light-sensitive materials processed exceeds a certain value, an increase in fog is caused.

This formation of fog is readily encountered in using developers in which the amount of iodine ions released from the light-sensitive material is large.

In order to overcome the above defects, particularly to improve stability during the development, several methods have been proposed. For example, Japanese Patent Publication No. 25691/77 and *Research Disclosure*, RD No. 18431, page 434 (Aug., 1979) describe the yellow fog-preventing effect due to addition of a nitron salt (1,4-diphenyl-3,5-endoanilino-4,5-dihydro-1,2,4-triazole). Japanese Patent Application (OPI) Nos. 87322/85, 117240/85, and 122936/85 disclose an improvement in dependency on halogen (e.g., iodine) ions contained in the processing solution through addition of a mesoionic triazolimine compound other than the nitron.

These methods, however, are not very effective, and rather cause serious desensitization. Thus, they are not satisfactory for practical use.

SUMMARY OF THE INVENTION

An object of the present invention is to provide a photographic light-sensitive material providing developed silver having a high covering power which is increased in development stability.

Another object of the present invention is to provide a photographic light-sensitive material providing developed silver having a high covering power which is increased in graininess.

It has now been found that the above objects can be attained by a silver halide photographic material comprising support bearing on at least one side thereof at least one silver halide photographic emulsion layer and at least one auxiliary layer, wherein the silver halide photographic emulsion layer is a layer made of a light-sensitive silver halide emulsion containing silver iodide and an internally fogged silver halide emulsion, or is composed of two layers independently containing the above emulsions, and the auxiliary layer contains substantially non-light-sensitive silver halide grains having an average grain size of not more than 0.5 μm.

Accordingly, the present invention relates to a silver halide photographic material comprising a support bearing on at least one side thereof at least one silver halide photographic emulsion layer and at least one auxiliary layer, wherein the silver halide photographic emulsion layer is a layer made of a light-sensitive silver halide emulsion containing silver iodide and an internally fogged silver halide emulsion, or is composed of a layer made of the light-sensitive silver halide emulsion containing silver iodide and a layer made of the internally fogged silver halide emulsion, and the auxiliary layer contains substantially non-light-sensitive silver halide grains having an average grain size of not more than 0.5 μm.

DETAILED DESCRIPTION OF THE INVENTION

The expression "light-sensitive" as used herein means that the sensitivity of a light-sensitive silver halide emulsion to visible light having a wavelength of from 400 to 700 nm is higher than that of the internally fogged silver halide emulsion, and more specifically the sensitivity to visible light of the light-sensitive silver halide emulsion is preferably at least 10 times, and more preferably at least 100 times, that of the internally fogged silver halide emulsion.

As the light-sensitive silver halide emulsion, a conventional silver halide emulsion, such as a surface latent image-type emulsion, is used.

The surface latent image-type silver halide emulsion is an emulsion in which the sensitivity when developed by the surface developing method (A) as described hereinafter after exposure of from 1 to 1/100 second is greater than that when developed by the internal developing method (B) as described hereinafter after exposure of from 1 to 1/100 second, and preferably the former sensitivity is at least two times the latter sensitivity. The sensitivity is defined as $$S = \frac{100}{Eh}$$

wherein S is sensitivity, and Eh is an exposure amount necessary to obtain an intermediate value of maximum density (Dmax) and minimum density (Dmin), i.e., ½(Dmax +Dmin).

SURFACE DEVELOPMENT (A)

Development is carried out at 20° C. for 10 minutes using a developer having the following formulation:

| N—Methyl-p-aminophenol (hemisulfate) | 2.5 g |
|---|---|
| Ascorbic acid | 10 g |
| Sodium metaborate 4-hydrate | 35 g |
| Potassium bromide | 1 g |
| Water to make | 1 liter |

INTERNAL DEVELOPMENT (B)

After treatment at about 20° C. for 10 minutes using a bleaching solution containing 3 g/l of red prussiate and 0.0126 g/l of phenosafranine, and washing with water is carried out for 10 minutes, and the development is then carried out using a developer having the following formulation:

| N—Methyl-p-aminophenol (hemisulfate) | 2.5 g |
|---|---|
| Ascorbic acid | 10 g |
| Sodium metaborate 4-hydrate | 35 g |
| Potassium bromide | 1 g |
| Sodium thiosulfate | 3 g |
| Water to make | 1 liter |

As the surface latent image-type silver halide, silver chloroiodide, silver iodobromide, and silver chloroiodobromide can be used. Preferably silver iodobromide is used. The silver iodide content is preferably from 1 to 30 mol% and especially preferably from 3 to 10 mol%. The average grain size is preferably greater than that of the internally fogged silver halide emulsion (i.e., silver halide emulsion the inside of which is fogged), and especially preferably at least 0.6 μm. The silver halide grains in the emulsion may have a regular crystal form such as cubic or octahedral form or irregular form such as spherical or plate-like (tabular) form, or a composite of grains having various crystal forms. Preferably used in the present invention are plate-like (tabular) grains in which the grain diameter is at least five times the thickness of the grain.

These plate-like (tabular) grains are described in detail by, for example, U.S. Pat. Nos. 4,434,226 and 4,434,227 and Japanese Patent Application (OPI) No. 127921/83.

The photographic light-sensitive emulsion as used herein can be prepared, for example, by the methods described in P. Glafkides, *Chimie et Physique Photographque*, Paul Montel Co. (1967), G. F. Duffin, *Photographic Emulsion Chemistry*, The Focal Press Co. (1966), and V. L. Zelikman et al., *Making and Coating Photographic Emulsion*, The Focal Press Co. (1964). That is, any of the acidic method, the neutral method, the ammonia method, and the like can be employed, and a soluble silver salt and a soluble halide can be mixed by any of the single jet method, the double jet method, or a combination thereof.

It is also possible to employ a method for forming silver halide grains in the presence of an excess of silver ions (i.e., so-called inverse jet method). In addition, a method in which the pAg of the liquid phase where silver halide is formed is maintained at a constant value, i.e., the so-called controlled double jet method, can also be employed.

The controlled double jet method permits preparation of a silver halide emulsion containing silver halide grains having a regular crystal form and a nearly uniform grain size.

Two or more silver halide emulsions prepared independently may be used in admixture with each other.

In the course of formation or physical ripening of silver halide grains during the preparation of the silver halide grains, cadmium salts, zinc salts, lead salts, thallium salts, iridium salts or complex salts thereof, rhodium salts or complex salts thereof, iron salts or complex salts thereof, and the like may be allowed to coexist.

As the light-sensitive silver halide emulsion, an emulsion not chemically sensitized, i.e., a so-called primitive emulsion can be used, but usually the emulsion is subjected to chemical sensitization. For this chemical sensitization, for example, the methods described in the above-cited references by P. Glafkides and V. L. Zelikman et al., and H. Frieser ed., *Die Grundlagen der Photographischen Prozesse mit Silber-halogeniden*, Akademische Verlagsgesellshaft (1968) can be used.

The sulfur sensitization method using compounds containing sulfur capable of reacting with silver ions or active gelatin, the reduction sensitization method using reducing substances, the noble metal sensitization method using noble metal (e.g., gold) compounds, and so forth can be used alone or in combination with each other.

Sulfur sensitizing agents which can be used include thiosulfates, thioureas, thiazoles, and rhodanines. Typical examples of the sulfur sensitizing agent are described in U.S. Pat. Nos. 1,574,944, 2,410,689, 2,278,947, 2,728,668, 3,656,955, 4,032,928, and 4,067,740.

Reduction sensitizing agents which can be used include stannous salts, amines, hydrazine derivatives, formamidinesulfinic acid, and silane compounds. Typical examples are described in U.S. Pat. Nos. 2,487,850, 2,419,974, 2,518,698, 2,983,609, 2,983,610, 2,694,637, 3,930,867, and 4,054,458.

For noble metal sensitization, as well as gold complex salts, the complex salts of Group VIII metals (e.g., platinum, iridium, and palladium) of the Periodic Table. Typical examples are described in U.S. Pat. Nos. 2,399,083 and 2,448,060 and British Pat. No. 618,061.

In the photographic light-sensitive material of the present invention, various hydrophilic colloids can be used as binders. Hydrophilic colloids commonly used in the field of photography, such as gelatin, colloidal albumin, polysaccharide, cellulose derivatives, and synthetic resins (e.g., polyvinyl compounds including polyvinyl alcohol derivatives, and polyacrylamide) can be used. In combination with such hydrophilic colloids, hydrophobic colloids such as dispersed vinyl polymers, particularly those increasing dimensional stability of the photographic material, can be used. Suitable examples of the compound of this type include water-insoluble polymers prepared by polymerization of vinyl monomers such as alkyl acrylates or methacrylates, acrylic acid, and sulfoaklyl acrylates or methacrylates.

To the above photographic light-sensitive emulsion can be added various compounds for the purpose of preventing a reduction in sensitivity or formation of fog during the process of preparation, storage or processing of the light-sensitive material. A large number of compounds have been known to be usable for this purpose, including, as well as 4-hydroxy-6-methyl-1,3,3a, 7-tetrazaindene, 3-methylbenzothiazole, and 1-phenyl-5-mercaptotetrazole, heterocyclic compounds, mercury-containing compounds, mercapto compounds, and metal salts.

Typical examples of the compound are described in K. Mees, *The Theory of the Photographic Process*, 3rd ed., (1966). In addition, antifoggants as described in Japanese Patent Application (OPI) Nos. 81024/74, 6306/75 and 19429/75, and U.S. Pat. No. 3,850,639, which are well known in the art, can be used.

As the internally fogged silver halide emulsion (i.e., silver halide emulsion the inside of which is fogged) that is used in the light-sensitive material of the present invention, an emulsion can be used which when coated on a transparent support in an amount (calculated as silver) of 2 $g/m^2$, and, without exposure, developed at 35° C. for 2 minutes with a developer D-19 (a developer produced by Eastman Kodak Co., which develops only a surface latent image of silver halide grains and which does not substantially have an internally developing ability), provides a transmitted fog density of not more than 0.5 (excluding the density of the support itself), and which when coated in the same manner as above and, without exposure, developed at 35° C. for 2 minutes with a developer resulting from addition of 0.5 g/l of potassium iodide to the developer D-19, provides a transmitted fog density of not less than 1.0 (excluding the density of the support itself).

The interally fogged silver halide emulsion can be prepared by various known techniques. For example, the method of U.S. Pat. No. 2,996,382 in which an emulsion having high internal light-sensitivity as described in U.S. Pat. No. 2,592,250 is fogged by irradiation with light; the core-shell emulsion method of U.S. Pat. No. 3,206,313 in which a core emulsion having fogged nuclei is first prepared by fogging under conditions of low pAg and high pH, or chemically fogging with, for example, a reducing agent, a gold compound or a sulfur-containing compound, and then a shell emulsion is precipitated around the core emulsion; the method of Japanese Patent Application (OPI) No. 215647/83 (which is substantially the same as the core-shell emulsion method of U.S. Pat. No. 3,206,313); and a method in which both the surface and inside of silver halide grains are fogged and then the fogged nuclei on the surface are bleached with, for example, a solution of red prussiate, can be employed.

The internally fogged silver halide emulsion has a smaller average grain size than the surface latent image-type silver halide emulsion. The average grain size of the internally fogged silver halide emulsion is preferably from 1.0 to 0.05 $\mu$m, more preferably from 0.6 to 0.1 $\mu$m, and especially preferably not more than 0.5 $\mu$m, providing good results.

The grain size of silver halide of the present invention indicates a diameter of a grain when the grain is spherical or nearly spherical, and when the grain is in another form such as cubic form, indicates a diameter of a sphere having the same volume as the grain.

As the internally fogged silver halide emulsion, any of silver bromide, silver iodobromide, silver iodochlorobromide, silver chlorobromide, silver chloride, and the like can be used.

The ratio of light-sensitive silver halide to internally fogged silver halide in the silver halide photographic material of the present invention can be changed by the type of the emulsion used (e.g., halogen composition), the type or application of the light-sensitive material used, the contrast of the emulsion used, and so forth. The above ratio is preferably from 100/1 to 1/100, and especially preferably from 10/1 to 1/10. The amount of silver coated is preferably from 0.5 to 10 $g/m^2$.

In the present invention, the light-sensitive silver halide emulsion and the internally fogged silver halide emulsion may be added to the same emulsion layer or to separate adjacent layers.

"Substantially non-light-sensitive silver halide grains" that are used in the present invention are incorporated in an auxiliary layer provided separately from the light-sensitive layer containing the silver halide grains. This auxiliary layer (e.g., a protective layer, an interlayer, and a filter layer) may be coated in any position in relation to other layers. It is preferable that the auxiliary layer be provided at the outside of a light-sensitive emulsion layer provided at the outermost position as seen from the support. Particularly desirably the auxiliary layer is provided so as to also act as a surface protective layer.

There are no special limitations to the amount of the above auxiliary layer coated. Usually it is provided so that the amount of the substantially non-light-sensitive silver halide grains coated is from $1 \times 10^{-6}$ to $1 \times 10^{-2}$ $mol/m^2$, and more preferably from $1 \times 10^{-4}$ to $1 \times 10^{-2}$ $mol/m^2$. It is preferred for the auxiliary layer to be coated so that the amount of the substantially non-light-sensitive silver halide grains coated is from 0.2 to 20 wt%, and especially preferably from 0.7 to 7 wt%, based on the total weight of light-sensitive silver halide.

Substantially non-light-sensitive silver halide grains used in the present invention are preferred to contain at least 75 mol% silver chloride. These silver halide grains may be of any composition as long as they are silver halide crystals containing silver chloride in the above-specified proportion. In particular, silver chloride, or silver chlorobromide or silver chloroiodobromide at least 75 mol% of which is silver chloride is preferred. Much preferred results can be obtained when silver chloride or silver chlorobromide containing at least 75 mol% of silver chloride is used. In the latter case, it is more preferred that the silver chloride content be at least 90 mol%. Thus silver chlorobromide having the above composition, particularly silver chloride is preferred.

The average grain size of the substantially non-light-sensitive silver halide grains is generally not more than 0.5 $\mu$m, preferably from 0.05 to 0.5 $\mu$m, and more preferably from 0.1 to 0.5 $\mu$m.

The substantially non-light-sensitive silver halide grains are not critical as to their form. They may be regular grains or irregular grains. In connection with dispersibility of the silver halide grains, they may be of multi-dispersion or of mono-dispersion.

The expression "substantially non-light-sensitive" is used herein to mean that the silver halide grains are relatively light insensitive as compared with the silver halide emulsion layer constituting the light-sensitive layer. More specifically, it is to be understood that when exposed to an amount of light necessary to sensitize light-sensitive silver halide constituting the light-sensitive material of the present invention, the silver halide grains are not substantially sensitized by such an amount of light energy. In more detail, it is preferred for the substantially non-light-sensitive silver halide grains to be such as to have a light sensitivity of 1/100 or less of that of the above light-sensitive silver halide grains.

Moreover it is desirable that the substantially non-light-sensitive silver halide grains be prepared in the presence of water-soluble rhodium at any desired point before completion of the first ripening (physical ripening) of the process for preparation of the silver halide emulsion. The grains thus prepared are particularly effective in reducing changes in photographic performance due to changes in stirring conditions of a developer.

Emulsions with a rhodium salt added thereto are described, for example, in British Pat. No. 775,197, U.S. Pat. No. 3,531,289, Japanese Patent Application (OPI) Nos. 125734/81, 149030/81, and 149031/81. Any of these emulsions are not used for the purpose of the present invention. Moreover a light-sensitive material in which the above emulsions are used is completely different from that of the present invention.

Typical examples of the water-soluble rhodium salt that is used in the present invention are rhodium chloride, rhodium trichloride, and rhodium ammonium chloride. In addition, their complex salts can be used. The rhodium salt may be added at any point before the first ripening during the process of preparation of the emulsion, but it is particularly preferred that the rhodium salt be added during the preparation of grains. The amount of the rhodium salt added is usually not less than $1 \times 10^{-6}$ mol, preferably not less than $1 \times 10^{-5}$ mol, and especially preferably from $5 \times 10^{-5}$ to $1 \times 10^{-3}$ mol.

The substantially non-light-sensitive silver halide grains of the present invention may have internally fogged nuclei, but preferably do not have fogged nuclei.

The substantially non-light-sensitive silver halide grains of the present invention may be used in the state that a sensitizing dye is adsorbed on the surface of the grains, or various other compounds are adsorbed in order to stabilize the performance. Useful sensitizing dyes are described, for example, in German Pat. No. 929,080, U.S. Pat. Nos. 2,493,748, 2,503,776, 2,519,001, 2,912,329, 2,656,959, 3,672,897, 3,694,217, 4,025,349, and 4,046,572, British Pat. No. 1,242,588, and Japanese Patent Publication Nos. 14030/69 and 24844/77.

These sensitizing dyes may be used alone or in combination with each other.

As compounds to stabilize the above performance (stabilizers), many compounds generally known as stabilizers such as azoles (e.g., benzothiazolium salts, nitroindazoles, triazoles, benzotriazoles, and benzimidazoles, particularly nitro- or halogen-substituted benzimidazoles), heterocyclic mercapto compounds (e.g., mercaptothiazoles, mercaptobenzothiazoles, mercaptobenzimidazoles, mercaptothiadiazoles, mercaptotetrazoles, particularly 1-phenyl-5-mercaptotetrazole, and mercaptopyrimidine), the above heterocyclic mercapto compounds further having a water-soluble group such as a carboxyl group and a sulfone group, thioketo compounds (e.g., oxazolinethione), azaindenes (e.g., tetrazaindenes, particularly 4-hydroxy-substituted (1,3,3a,7)tetrazaindenes), benzenethiosulfonic acids, and benzenesulfinic acid can be used. These compounds can be absorbed on the surface of silver halide grains substantially not having light sensitivity for the purpose of, e.g., stabilizing performance.

Of these stabilizers, heterocyclic mercapto compounds are preferably used. Particularly preferred are compounds represented by formula (I)

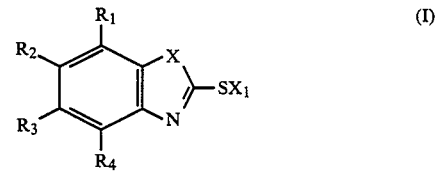

wherein X is —O—, —NH— or —S—; $R_1$, $R_2$, $R_3$, and $R_4$ each represents a hydrogen atom or a group which can be substituted, and at least one of $R_1$, $R_2$, $R_3$, and $R_4$ is a substituted or unsubstituted alkyl or aryl group having 13 carbon atoms or less which is linked, directly or through a divalent connecting group, to the benzene nucleus; and $X_1$ represents a hydrogen atom or a cation necessary for rendering the molecule neutral.

Formula (I) is hereinafter explained in further detail.

In formula (I), X is —O—, —NH— or —S—, and especially preferably, X is —NH—.

$R_1$, $R_2$, $R_3$, and $R_4$ are each a hydrogen atom or a group which can be substituted. Preferred examples for $R_1$, $R_2$, $R_3$, and $R_4$ are a hydrogen atom, a halogen atom (e.g., F, Cl and Br), a substituted or unsubstituted alkyl group (e.g., a methyl group, a trifluoromethyl group, an ethyl group, an n-octyl group, and a benzyl group), a substituted or unsubstituted aryl group (e.g., a phenyl group and a p-chlorophenyl group), a substituted or unsubstituted alkoxy or aryloxy group (e.g., a methoxy group, an n-hexyloxy group, a phenoxy group, an n-octyloxy group, and a 2-ethylhexyloxy group), a sulfonyl group (e.g., a methanesulfonyl group and a p-toluenesulfonyl group), a sulfonamido group (e.g., an n-octanesulfonamido group and a p-toluenesulfonamido group), a sulfamoyl group (e.g., a diethylsulfamoyl group and a 4-chlorophenylsulfamoyl group), a carbamoyl group (e.g., an n-butylcarbamoyl group, a 4-cyanophenylcarbamoyl group, and a 2-ethylhexylcarbamoyl group), an amido group (e.g., an n-hexaneamido group, an n-decaneamido group, a benzamido group, and a 2-ethylhexanoylamino group), a ureido group (e.g., a 3-butylureido group and a morpholinocarbonylamino group), an aryloxycarbonylamino or alkoxycarbonylamino group (e.g., an ethoxycarbonylamino group, an isobutylcarbonylamino group, and a phenoxycarbonylamino group), an aryloxycarbonyl or alkoxycarbonyl group (e.g., an ethoxycarbonyl group and a phenoxycarbonyl group), an arylaminocarbonyloxy or alkylaminocarbonyloxy group (e.g., a phenylaminocarbonyloxy group and an isobutylaminocarbonyloxy group), a cyano group, and an alkylthio or arylthio group (e.g., an n-octylthio group and a 2-methoxycarbonylphenylthio group). These groups which can be substituted preferably have 13 carbon atoms or less, and more preferably 11 carbon atoms or less.

At least one of $R_1$, $R_2$, $R_3$, and $R_4$ is a substituted or unsubstituted alkyl or aryl group having 13 carbon atoms or less, and preferably a substituted or unsubstituted alkyl group having from 5 to 11 carbon atoms, which is linked, directly or through a divalent connecting group, to the benzene nucleus. Particularly preferred examples of the divalent connecting group are an amido bond, a sulfonamido bond, a ureido bond, an ether bond, a thioether bond, a sulfonyl bond, a carbonyl bond, a urethane bond, a carbamoyl bond, and a sulfamoyl bond.

$X_1$ represents a hydrogen atom or a cation necessary for rendering the molecule neutral (e.g., Na, K, and $NH_4$).

Typical examples of compounds of formula (I) which are used in the present invention are shown below although the present invention is not limited thereto.

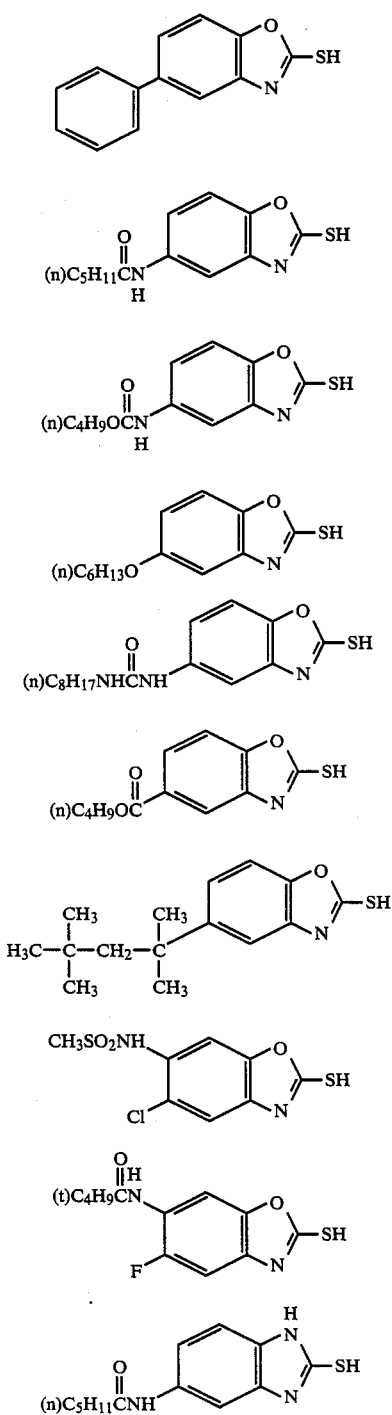

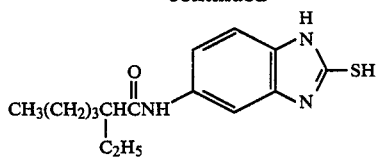

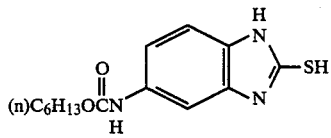

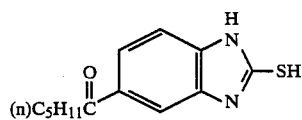

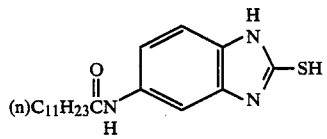

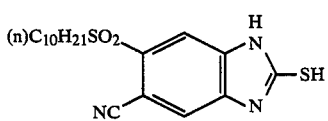

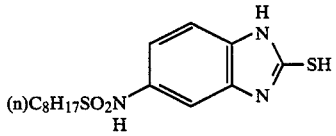

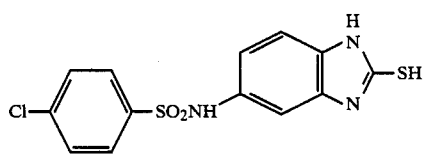

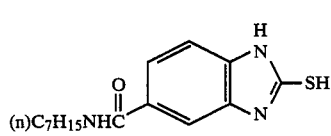

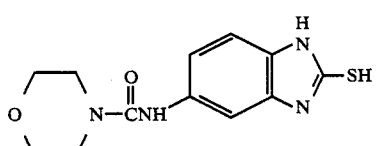

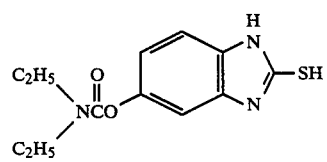

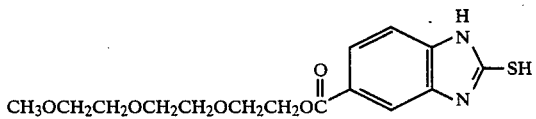

-continued

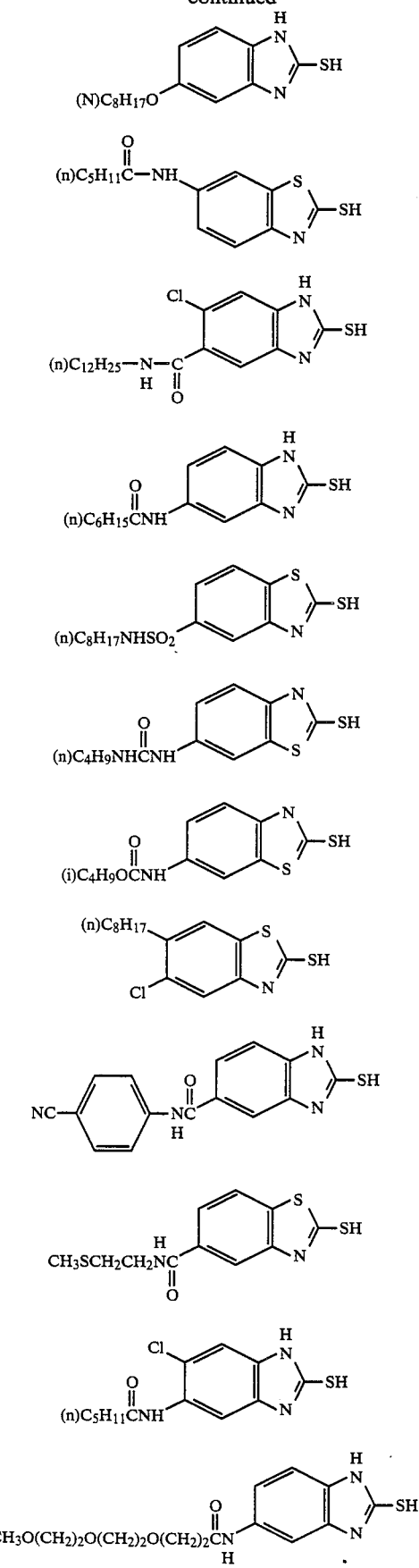

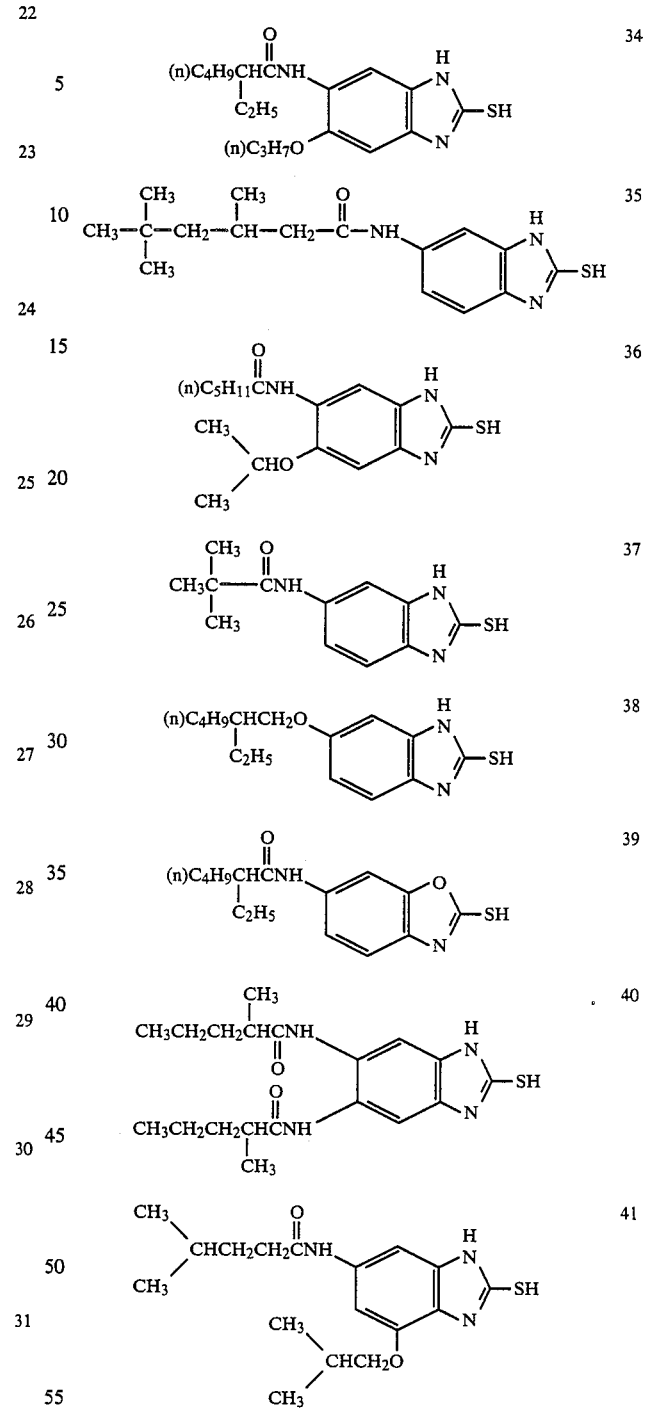

The compounds represented by formula (I) can be prepared by the methods described in J. Van Allan, B. D. Deacon, *Org. Synth.*, Vol. IV, p. 569 (1963), J. Bunner, *Ber.*, 45, p. 2390 (1923), and the following typical preparation examples.

PREPARATION EXAMPLE 1

Preparation of Compound 10

8.3 g of 5-amino-2-mercaptobenzoimidazole was dissolved in 120 ml of pyridine, and 6.7 g of hexanoyl chloride was added dropwise thereto while cooling with ice. The resulting mixture was stirred for 2 hours at room temperature. Upon addition of 800 ml of ice water, crystals precipitated. These crystals were separated by filtration and recrystallized from a mixed solvent (10:1) of ethanol and water. The yield was 7.8 g and the melting point was 262°–264° C.

PREPARATION EXAMPLE 2

Preparation of Compound 14

8.3 g of 5-amino-2-mercaptobenzoimidazole was dissolved in 120 ml of pyridine, and 12 g of lauroyl chloride was added dropwise thereto while cooling with ice. The resulting mixture was stirred for 3 hours at room temperature and then 800 ml of ice water was added. Crystals precipitated were separated by filtration and recrystallized from a mixed solvent (10:1) of methanol and water. The yield was 10.2 g and the melting point was 266°–267° C.

PREPARATION EXAMPLE 3

Preparation of Compound 18

5.8 g of 5-carboxy-2-mercaptobenzoimidazole was added to 60 ml of DMF (dimethylformamide), and 6.3 ml of triethylamine and then 4.3 ml of ethyl chloroformate were added dropwise thereto while cooling with ice.

The resulting mixture was stirred for 30 minutes while cooling with ice, and then 5.2 g of heptylamine was added dropwise and stirred for 4 hours. The reaction mixture was added to a solution of 3 g of sodium bicarbonate in 500 ml of water, and the precipitate thus formed was recrystallized from ethyl acetate. The yield was 3.8 g and the melting point was 230°–232° C.

PREPARATION EXAMPLE 4

Preparation of Compound 22

4.7 g of p-octyloxy-o-phenylenediamine was added to 60 ml of an ethanol solution of 1.2 g of potassium hydroxide, and 6 ml of carbon disulfide was added dropwise thereto at 50° C.

The resulting mixture was further refluxed for 4 hours and then added to 150 ml of ice water, and then 3 ml of concentrated hydrochloric acid was added thereto while stirring. The precipitate thus obtained was separated by filtration and recrystallized from acetonitrile. The yield was 3.7 g and the melting point was 230°–232° C.

PREPARATION EXAMPLE 5

Preparation of Compound 23

9.1 g of 6-amino-2-mercaptobenzothiazole was added to 70 ml of pyridine, and 6.7 g of hexanoyl chloride was added dropwise thereto while cooling with ice. The resulting mixture was stirred for 3 hours at room temperature and then 800 ml of ice water was added thereto. Crystals precipitrated were collected by filtration and then recrystallized from a mixed solvent (10:1) of ethanol and water. The yield was 6.9 g and the melting point was 179°–180° C.

The compound of formula (I) can be used in an amount of from $1 \times 10^{-3}$ to 10 mols per mol of silver halide grain in the auxiliary layer. Preferably the compound of formula (I) is added in an amount of from $1 \times 10^{-2}$ to 1 mol per mol of silver halide grain in the auxiliary layer. Most preferably the amount of the compound of formula (I) being added is in the neighborhood of the saturated adsorpotion amount on the surface of the internally fogged grains. In adding the compound of formula (I), it may be dispersed directly in a hydrophilic colloid, or after being dissolved in an organic solvent such as methanol or ethylene glycol, it may be added.

In a case that both the internally fogged silver halide emulsion and light-sensitive silver halide emulsion are present in the same emulsion layer, it is preferred that the compound of formula (I) be added to the internally fogged silver halide emulsion and adsorbed thereon before mixing them.

The light-sensitive material of the present invention may take several layer structures. Typical examples are shown below.

(1) A light-sensitive material comprising a support, an emulsion layer containing a light-sensitive silver halide containing silver iodide and an internally fogged silver halide, provided on the support, and an auxiliary layer (protective layer) provided on the emulsion layer.

(2) A light-sensitive material of the same structure as (1) above, wherein an emulsion layer containing a light-sensitive silver halide is further provided between the emulsion layer and the auxiliary layer (protective layer).

(3) A light-sensitive material comprising a support, an emulsion layer containing an internally fogged silver halide provided on the support, an emulsion layer containing a light-sensitive silver halide containing silver iodide provided on the above emulsion layer, and an auxiliary layer (protective layer) provided on the latter emulsion layer.

In the above layer structures, the auxiliary layer acts as a protective layer and this protective layer contains the substantially non-light-sensitive silver halide grains. Of course, the auxiliary layer of the present invention may be provided separately from the protective layer.

The above layer assembly may be provided not only on one side of the support but also on both sides of the support.

A protective layer of the light-sensitive material of the present invention is made of hydrophilic colloid. As such hydrophilic colloids, the colloids as described above can be used. The protective layer may be of a single layer structure or of a multi-layer structure.

A matting agent and/or a lubricant may be added to the emulsion layer or the protective layer of the light-sensitive material of the present invention. It is preferred that the matting agent and/or lubricant be added to the protective layer.

Preferred examples of the matting agent are organic compounds such as water-dispersible vinyl polymers (e.g., polymethyl methacrylate) or inorganic compounds such as silver halide and strontium barium sulfate, having a suitable grain diameter (preferably a grain diameter of from 0.3 to 5 $\mu$m or of at least two times, and particularly preferably at least four times, the thickness of the protective layer).

The lubricant is effective in preventing adhesion failure, like the matting agent, and, furthermore, is effective in improving friction characteristics related to camera suitability at the time of photographing or projection of a movie film. Preferred examples of the lubricant are waxes such as liquid paraffin and higher fatty acid esters, fluorinated hydrocarbon polymers or their derivatives, and silicones such as polyalkylpolysiloxanes, polyarylpolysiloxanes, polyalkylarylpolysiloxanes, and their alkylene oxide adducts.

In the light-sensitive material of the present invention, if desired, an antihalation layer, an interlayer, a filter layer and so forth may be provided.

The photographic silver halide emulsion layer and other hydrophilic colloid layer of the light-sensitive material of the present invention can be hardened using suitable hardening agents. Hardening agents which can be used include vinylsulfonyl compounds as described in Japanese Patent Application (OPI) Nos. 76025/78, 76026/78, and 77619/78, hardening agents containing active halogen, dioxane derivatives, and hydroxypolysaccharides such as hydroxystarch.

To the photographic silver halide emulsion layer, other additives, particularly those useful for the emulsion, such as a lubricant, a sensitizing agent, a light-absorbing dye, and a platicizer can be added.

In addition, compounds releasing iodine ion, such as potassium iodide, can be added to the silver halide emulsion. A desired image can be obtained using a developer containing iodine ions.

In the light-sensitive material of the present invention, water-soluble dyes may be added to the hydrophilic colloid layer as filter dyes or for various purposes, e.g., preventing irradiation and halation. Such water-soluble dyes include oxonol, hemioxonol, styryl, merocyanine, cyanine and azo dyes. Of these dyes, oxonol, hemioxonol and merocyanine dyes are particularly useful.

In the light-sensitive material of the present invention, when the hydrophilic colloid layer contains additives such as dyes, and ultraviolet light absorbing agents, these additives may be mordanted, for example, with cationic polymers.

The light-sensitive material of the present invention may contain surface active agents for various purposes. Any of nonionic, ionic and amphoteric surface active agents can be used depending on the purpose. For example, polyoxyalkylene derivatives and amphoteric aminoacids (including sulfobetaines) can be used. Typical examples of such surface active agents are described in U.S. Pat. Nos. 2,600,831, 2,271,622, 2,271,623, 2,275,727, 2,787,604, 2,816,920, and 2,739,891 and Belgian Pat. No. 652,862.

In the light-sensitive material of the present invention, the photographic emulsion may be spectrally sensitized to blue, green, red, or infrared light of relatively long wavelength, using sensitizing dyes. Sensitizing dyes which can be used for this purpose include cyanine, merocyanine, complex cyanine, complex merocyanine, holopolar cyanine, styryl, hemicyanine, oxonol, and hemioxonol dyes.

The sensitizing dye that is used in the present invention is used in the same concentration as in conventional negative-type silver halide emulsions. It is particularly advantageous that the sensitizing dye be used within a concentration range substantially not causing a decrease in the inherent sensitivity of the silver halide emulsion. The amount of the sensitizing dye used is generally from about $1.0 \times 10^{-5}$ to $5 \times 10^{-4}$ mol, and preferably from about $4 \times 10^{-5}$ to $2 \times 10^{-4}$ mol, per mol of the silver halide.

In the light-sensitive material of the present invention, the photographic emulsion layer and other layers are provided on one side or both sides of a flexible support commonly used in preparation of the usual photographic light-sensitive material. Useful examples of the flexible support are films of synthetic polymers such as cellulose acetate, cellulose acetate butyrate, polystyrene, and polyethylene terephthalate, and paper coated or laminated with a baryta layer or α-olefin polymers (e.g., polyethylene, polypropylene, and an ethylene/butene copolymer).

In the light-sensitive material of the present invention, the photographic emulsion layer and other hydrophilic colloid layer can be coated on a support or other layer by various known coating techniques such as dip coating, roller coating, curtain coating, and extrusion coating.

The light-sensitive material of the present invention can be used as any type of light-sensitive material requiring high sensitivity or high contrast. For example, it can be used as an X-ray photographic light-sensitive material, a lith-type photographic light-sensitive material, a black-and-white negative photographic light-sensitive material, a color negative light-sensitive material, or a color paper light-sensitive material.

In addition, the light-sensitive material of the present invention can be used as a diffusion transfer light-sensitive material in which undeveloped silver halide is dissolved and precipitated in an image-receiving layer in adjacent relation to a silver halide emulsion layer to thereby form a positive image, or a color diffusion transfer light-sensitive material of the same mechanism as above.

Photographic processing of the light-sensitive material of the present invention can be carried out using known processing methods and known processing solutions as described in, for example, *Research Disclosure*, RD No. 17643, pp. 28-40 (Dec. 1978). Depending on the purpose, the photographic processing may be a photographic processing to form a silver image (black-and-white photographic processing) or a photographic processing to form a dye image (color photographic processing). The processing temperature is chosen within the temperature of from 8° to 50° C. Lower temperatures than 18° C. or higher temperatures than 50° C. can be employed.

The developer for use in the black-and-white photographic processing, for example, may contain known developing agents. These developing agents include dihydroxybenzenes (e.g., hydroquinone), 3-pyrazolidones (e.g., 1-phenyl-3-pyrazolidone), and aminophenols (e.g., N-methyl-p-aminophenol). The developing agents can be used alone or in combination with each other.

In photographic processing of the light-sensitive material of the present invention, a developer containing imidazoles as silver halide solvents as described in Japanese Patent Application (OPI) No. 78535/72 can be used. In addition, a developer containing a silver halide solvent and an additive such as an indole or a triazole as described in Japanese Patent Application (OPI) No. 37643/83 can be used.

The developer usually contains other known additives, such as a preservative, an alkali agent, a pH buffer, and an antifoggant, and if desired, may further contain a dissolving aid, a color-controlling agent, a development accelerator, a surface active agent, a defoaming agent, a hard water-softening agent, a hardening agent, a tackifier, and the like.

To the photographic emulsion of the present invention can be applied so-called "lith-type" development. This "lith-type" development is a processing in which for photographic reproduction of a line image or photographic reproduction in a dot form of a half tone image, development is carried out using dihydroxybenzenes as the developing agent and at a low sulfite ion concentration. Details are described in Mason, *Photographic Processing Chemistry*, pp. 163-165 (1966), by The Focal Press Co., London.

As a special type of development, there may be employed a method in which a developing agent is incorporated in the light-sensitive material, for example, in the emulsion layer, and the light-sensitive material is developed by treating in an aqueous alkali solution. Hydrophobic developing agents can be incorporated in the emulsion layer by various methods as described in *Research Disclosure*, RD No. 16928 (May, 1978), U.S. Pat. No. 2,739,890, British Pat. No. 813,253, and West German Pat. No. 1,547,763. This developing method can be performed in combination with silver salt stabilization using thiocyanic acid salts.

In the present invention, a fixer having a commonly used composition can be used. Fixing agents which can be used include, as well as thiosulfates and thiocyanates, organic sulfur compounds which are known to be effective as fixing agents. The fixer may contain a water-soluble aluminum salt as a hardening agent.

The present invention is described in greater detail with reference to the following non-limiting examples.

EXAMPLE 1

(1) Preparation of Light-Sensitive Silver Halide Emulsion

A thick plate-like (tabular) silver iodobromide emulsion (AgI=4 mol%) having an average grain diameter of 1.0 $\mu$m was prepared from an aqueous silver nitrate solution, an aqueous potassium bromide solution and an aqueous potassium iodide solution by the usual ammonia method while maintaining the concentration of KBr in a container containing halogen and gelatin prior to addition at a relatively high level. The emulsion thus prepared was washed by the usual precipitation method and chemically sensitized by the gold/sulfur sensitization method using chloroauric acid and sodium thiosulfate, and then 4-hydroxy-6-methyl-1,3,3a,7-tetrazaindene was added thereto as a stabilizer to obtain a light-sensitive silver iodobromide emulsion (Emulsion A).

(2) Preparation of Internally Fogged Fine Grain Emulsion

A silver chloroiodobromide (Emulsion B) having an average grain diameter of 0.3 $\mu$m the sensitivity of which was adjusted to about 1/100 that of the emulsion A and the inside of which was fogged was prepared by the method described in U.S. Pat. No. 2,592,250.

(3) Preparation of Emulsion Coating Solution

Five parts of the Emulsion A and 1 part of the Emulsion B were mixed, and then a dodecylbenzenesulfonic acid salt as a coating aid, and potassium p-vinylbenzenesulfonate and a mesoionic triazolimine compound as tackfiers were added thereto to prepare a coating solution. The weight ratio of silver to gelatin was 1.15/1.

(4) Preparation of Silver Chlorobromide Fine Grain Emulsion

Small amounts of NaCl, water and gelatin were placed in a reactor and treated by the double jet method to prepare an aqueous AgNO$_3$ solution. Nearly equimolar amounts of the aqueous AgNO$_3$ solution and an aqueous solution of a mixture of NaCl and KBr (ratio of Br$^\ominus$ to Cl$^\ominus$ = 5:95) were added at a constant flow rate to prepare grains having an average grain size (calculated as a spherical grain) of 0.1 $\mu$m. These grains were washed with water by the usual precipitation method and then redispersed gelatin was added thereto to prepare an emulsion.

Three types of emulsions having the same composition as above, but having different average grain sizes of 0.2 $\mu$m, 0.3 $\mu$m and 0.6 $\mu$m were prepared in the same manner as above, except that the grain formation temperature and the amount of NaCl were changed.

(5) Preparation of Coating Solution For Surface Protective Layer (Auxiliary Layer)

An 8 wt % aqueous gelatin solution containing polyacrylamide, dextran, a tackifier (sodium polystyrenesulfonate), a matting agent (polymethyl methacrylate fine grains; average grain size: 3.0 $\mu$m), a hardening agent (N,N'-ethylenebis-(vinylsulfonylacetamide)), a coating aid (sodium t-octylphenoxyethoxyethoxyethane sulonate), and an antistatic agent (polyoxyethylene-based surface active agent), the total weight of the above additives being about 20 wt % of the gelatin, was prepared. Silver chlorobromide fine grain emulsions having the same halogen composition (Cl/Br=95/5) but different average grain sizes as shown in Table 1 were each added to the above aqueous gelatin solution to prepare a coating solution for the protective layer.

(6) Preparation of Coated Sample

The above coating solution was coated on both sides of a polyethylene terephthalate support in such a manner that the amount of silver coated on one side was 2.5 g/m$^2$. Simultaneously with the coating of the emulsion coating solution, the coating solution for the surface protective layer was coated on both sides of the support in such a manner that the amount of silver chlorobromide fine grains coated per surface was as shown in Table 1, and the amount of gelatin coated was 0.05 g/m$^2$ (per surface), to prepare light-sensitive material sample Nos. 2 to 7.

As a control sample, a light-sensitive material was prepared in the same manner as above, except not using the AgBrCl fine grain emulsion but rather using the coating solution (5) (light-sensitive material sample No. 1).

(7) Sensitometry

The light-sensitive materials were allowed to stand for 7 days under conditions of temperature 25° C. and relative humidity 65%. Then each material was exposed to blue light of from 360 to 480 nm having an intensity peak at 414 nm, and then developed at 35° C. for 25 seconds and fixed using the following developer (A) and fixer.

| Developer (A) | |
| --- | --- |
| 1-Phenyl-3-pyrazolidone | 1.5 g |
| Hydroquionone | 30.0 g |
| 5-Nitroimidazole | 0.25 g |
| KBr | 3.7 g |
| Anhydrous sodium sulfite | 20.0 g |
| Boric acid | 10.0 g |
| 25% Aqueous solution of glutaraldehyde | 20 ml |
| Water to make | 1 liter |
| (The pH was adjusted to 10.2.) | |
| Fixer | |
| Ammonium thiosulfate | 200.0 g |
| Sodium sulfite (anhydrous) | 20.0 g |
| Boric acid | 8.0 g |
| Sodium ethylenediaminetetraacetate | 0.1 g |
| Aluminum sulfate | 15.0 g |
| Sulfuric acid | 2.0 g |
| Glacial acetic acid | 22.0 g |
| Water to make | 1.0 liter |
| (The pH was adjusted to 4.2.) | |

The processed photographic materials were subjected to the sensitometry. The results are shown in Table 1.

To the developer (A) was added 30 mg/l of KI, and development was performed at 35° C. for 25 minutes. Then the value of fog was measured.

TABLE 1

| | AgClBr Fine Grain in Surface Protective Layer | | | | | | | | |
|---|---|---|---|---|---|---|---|---|---|
| Run No. | Average Grain size (μm) | Cl/Br Molar Ratio | Coated Amount (g-Ag/m² per one surface) | Photographic Characteristics | | | Amount of KI released in Developer (B) (mg/l) | Fog when using Developer containing KI | Remarks |
| | | | | Relation Sensitivity | Gradation (γ) | Graininess | | | |
| 1 | — | — | — | 100 | 3.09 | 1 | 53.4 | 0.24 | Comparative Example |
| 2 | 0.1 | 95/5 | 0.05 | 98 | 2.60 | 4 | 22.0 | 0.05 | Example of the Present Invention |
| 3 | 0.2 | 95/5 | 0.05 | 99 | 2.65 | 4 | 24.0 | 0.06 | " |
| 4 | 0.3 | 95/5 | 0.05 | 100 | 2.70 | 4 | 27.0 | 0.07 | " |
| 5 | 0.6 | 95/5 | 0.05 | 101 | 3.02 | 1 | 49.5 | 0.23 | Comparative Example |
| 6 | 0.6 | 95/5 | 0.10 | 98 | 2.95 | 2 | 44.0 | 0.19 | " |
| 7 | 0.6 | 95/5 | 0.15 | 98 | 2.85 | 3 | 40.0 | 0.17 | " |

In Table 1, the value of sensitometry is the reciprocal of an exposure amount necessary to obtain a transmitted light blackening density of fog +0.3, and is indicated as a relative value with the sensitivity of the sample No. 1 taken as 100. The gamma value is indicated at the gradient of a characteristic curve between densities of fog +0.25 and fog +2.0.

The samples were measured for graininess and rated as follows:
5: Very good
4: Good
3: Unsuitable for practical use
2: Bad
1: Very bad;

Each light-sensitive material corresponding to 12pieces of printing papers having a size of 10×12 in. was exposed to white light and then continuously developed at 20° C. for 4 minutes with a developer (B) having the formulation shown below. Then the amount of iodine ions released into the developer was measured.

| Developer (B) | |
|---|---|
| 1-Phenyl-3-pyrazolidone | 0.5 g |
| Hydroquinone | 20.0 g |
| Sodium ethylenediaminetetraacetate | 2.0 g |
| Potassium sulfite | 60.0 g |
| Boric acid | 4.0 g |
| Potassium carbonate | 20.0 g |
| Sodium bromide | 5.0 g |
| Diethylene glycol | 30.0 g |
| Water to make | 1 liter |
| (The pH was adjusted to 10.0 with NaOH.) | |

It can be seen from Table 1 that when an AgClBr fine grain emulsion (molar ratio of $Cl^\ominus$ to $Br^\ominus$ is 95/5) is added to the surface protective layer, if the grain size is 0.6 μm, graininess and processing solution stability are improved only insufficiently. Even if the amount of the emulsion coated is increased, the characteristics of graininess and processing solution stability are improved insufficiently although they are improved to a certain extent; rather, this leads to an increase in the amount of silver coated, resulting in a serious reduction in the effect of high covering power (cp), for example (Sample Nos. 5 to 7). On the other hand, if an AgClBr fine grain emulsion having a $Cl^\ominus/Br^\ominus$ molar ratio of 95/5 and a grain size of not more than 0.5 μm according to the present invention is added to the surface protective layer, very good gradation, and good graininess and processing solution stability can be obtained (Sample Nos. 2 to 4).

EXAMPLE 2

The same surface light-sensitive Emulsion A and internally fogged Emulsion B as used in Example 1 were prepared, and an emulsion coating solution was prepared using them in the same manner as in Example 1. A silver chlorobromide fine grain emulsion to be added to the surface protective layer was prepared in the same manner as in Example 1 except that a methanol solution of Compound 11 or Compound 29 among of the compounds of formula (I) was added and adsorbed on the surface of grains.

The results are shown in Table 2.

TABLE 2

| | AgClBr Fine Grains in Surface Protective Layer | | | | | | | | | |
|---|---|---|---|---|---|---|---|---|---|---|
| Run No. | Average Grain Size (μm) | Cl/Br Molar Ratio | Absorbed Compound | | Coated Amount (g-Ag/m² per one surface) | Photographic Characteristics | | | Amount of KI released in Developer B (mg/l) | Fog when using Developer containing KI | Remarks |
| | | | Type | Amount (mol/mol Ag) | | Relative Sensitivity | Gradation (γ) | Graininess | | | |
| 11 | 0.2 | 95/5 | — | — | 0.05 | 99 | 2.60 | 4 | 22.0 | 0.05 | Example of the Present Invention |
| 12 | " | " | No. 11 | 0.05 | " | 100 | 2.55 | 4 | 20.0 | 0.04 | " |
| 13 | " | " | " | 0.20 | " | 98 | 2.51 | 5 | 18.5 | 0.03 | " |
| 14 | " | " | No. 29 | 0.05 | " | 99 | 2.54 | 4 | 20.2 | 0.04 | " |
| 15 | " | " | " | 0.20 | " | 100 | 2.49 | 5 | 15.7 | 0.03 | " |

It can be seen from the results of Table 2 that if a compound of formula (I) is adsorbed on silver halide grains contained in the surface protective layer, the amount of iodide released in the developer is decreased with almost no reduction in photographic characteristics of sensitivity, gradation, and graininess, and, furthermore, the effect of iodide in the developer on photographic properties is decreased.

EXAMPLE 3

The same surface light-sensitive emulsion A and silver chlorobromide emulsion to be added to the surface protective layer as in Example 1 were used, but as the internally fogged fine silver halide grain emulsion, the following was used.

An aqueous solution of silver nitrate and an aqueous solution of a mixture of sodium bromide and sodium chloride were added at the same time to a 2 wt % aqeuous solution of gelatin while stirring at 55° C. to prepare core grains. The temperature was raised to 75° C., and suitable amounts of sodium hydroxide and silver nitrate were added. The resulting mixture was ripened for 15 minutes to form fogged nuclei on the core grains. The temperature was lowered to 55° C., and acetic acid and potassium bromide were added to return the pH and pAg to 6.5 and 8.1, respectively. Then an aqueous solution of silver nitrate and an aqueous solution of a mixture of potassium bromide and sodium chloride were added at the same time. Desalting was conducted by conventional coagulation. The resulting mass was redispersed in a gelatin solution to prepare an internally fogged silver chlorobromide emulsion (Emulsion C) having an average grain size of 0.37 μm (AgCl: 10 mol %). The Emulsions A and C were mixed in a ratio of 5 parts to 1 part and then processed in the same manner as in Example 1 to prepare a coating solution.

Thereafter the procedure of Example 1 was repeated. It was confirmed that the sample of the present invention has good gradation, and graininess and processing solution stability as in the case of Sample Nos. 2 to 4 and 9 to 10 in Example 1.

The photographic light-sensitive material of the present invention produces an image which is superior in both gradation and graininess, and even though a high iodide content emulsion is used as the light-sensitive silver halide emulsion, exhibits good processing solution stability during the process of development. Particularly when a compound of formula (I) is adsorbed on silver halide grains in the auxiliary layer (surface protective layer), the release of iodide to the developer can be greatly decreased. Thus, the effect of iodide accumulating in the developer on photographic properties is reduced, and the development can be carried out in a more stabilized manner.

While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising a support bearing on at least one side thereof at least one silver halide photographic emulsion layer and at least one auxiliary layer, wherein the silver halide photographic emulsion layer is a layer made of a light-sensitive silver halide emulsion containing silver iodide and an internally fogged silver halide emulsion, or is composed of a layer made of the light-sensitive silver halide emulsion containing silver iodide and a layer made of the internally fogged silver halide emulsion, and the auxiliary layer contains substantially non-light-sensitive silver halide grains having an average grain size of not more than 0.5μm and is provided outside of and on the same side of the support as a light sensitive emulsion layer which is the outermost light-sensitive emulsion layer from the support, and wherein the amount of the substantially non-light-sensitive silver halide grains coated is from $1 \times 10^{-4}$ to $1 \times 10^{-2}$ mol/m² and wherein said silver halide photographic material contains no metallic salts coated with a less solubilizing agent, wherein the substantially non-light-sensitive silver halide grains comprise at least 75 mol % silver chloride, and have absorbed on the surface thereof at least one compound represented by formula (I)

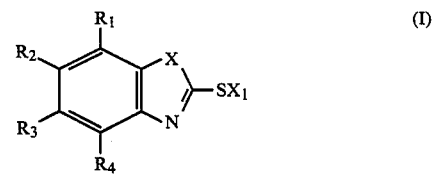

wherein X is —O—, —NH— or —S—; $R_1$, $R_2$, $R_3$ and $R_4$ each represents a hydrogen atom or a substituted group, at least one of $R_1$, $R_2$, $R_3$ and $R_4$ being a substituted or unsubstituted alkyl or aryl group having 13 carbon atoms or less which is linked, directly or through a divalent connecting group, to the benzene nucleus of formula (I); and $X_1$ represents a hydrogen atom or a cation necessary for rendering the molecule neutral.

2. A silver halide photographic material as in claim 1, wherein X is —NH—, and $R_1$, $R_2$, $R_3$, and $R_4$ each represents a hydrogen atom, a halogen atom, a substituted or unsubstituted alkyl group, a substituted or unsubstituted aryl group, a substituted or unsubstituted alkoxy or aryloxy group, a sulfonyl group, a sulfonamido group, a sulfamoyl group, a carbamoyl group, an amido group, a ureido group, an aryloxycarbonylamino or alkoxycarbonylamino group, an aryloxycarbonyl or alkoxycarbonyl group, an arylaminocarbonyloxy or alkylaminocarbonyloxy group, a cyano group, or an alkylthio or arylthio group.

3. A silver halide photographic material as in claim 1, wherein the substantially non-light-sensitive silver halide grains are coated in an amount of from 0.2 to 20 wt % based on the total weight of the light-sensitive silver halide.

4. A silver halide photographic material as in claim 1, wherein the substantially non-light-sensitive silver halide grains are coated in an amount of from 0.7 to 7 wt % based on the total weight of the light-sensitive silver halide.

5. A silver halide photographic material as in claim 1, wherein said light-sensitive silver halide emulsion containing silver iodide has a sensitivity to visible light of at least 10 times that of said internally fogged silver halide emulsion.

6. A silver halide photographic material comprising a support bearing on at least one side thereof at least one silver halide photographic emulsion layer and at least one auxiliary layer, wherein the silver halide photographic emulsion layer is a layer made of a light-sensitive silver halide emulsion containing silver iodide and an internally fogged silver halide emulsion, or is composed of a layer made of the light-sensitive silver halide emulsion containing silver iodide and a layer made of the internally fogged silver halide emulsion, and the auxiliary layer contains substantially non-light-sensitive silver halide grains having an average grain size of not more than 0.582 m and is provided outside of and on the same side of the support as a light sensitive emulsion layer which is the outermost light-sensitive emulsion layer from the support, and wherein the amount of the substantially non-light-sensitive silver halide grains coated is from $1\times10^{-4}$ to $1\times10^{-2}$ mol/m$^2$ and wherein said silver halide photographic material contains no metallic salts coated with a less solubilizing agent, wherein said light-sensitive silver halide emulsion containing silver iodide has a sensitivity to visible light of at least 100 times that of said internally fogged silver halide emulsion.

7. A silver halide photographic material as in claim 1, wherein the light-sensitive silver halide is silver iodobromide.

8. A siver halide photographic material as in claim 1, wherein said internally fogged silver halide emulsion has an average grain size of from 1.0 to 0.05μm.

9. A silver halide photographic material as in claim 1, wherein said substantially non-light-sensitive silver halide grains have an average grain size of not more than 0.5μm.

10. A silver halide photographic material comprising a support bearing on at least one side thereof at least one silver halide photographic emulsion layer and at least one auxiliary layer, wherein the silver halide photographic emulsion layer is a layer made of a light-sensitive silver halide emulsion containing silver iodide and an internally fogged silver halide emulsion, or is composed of a layer made of the light-sensitive silver halide emulsion containing silver iodide and a layer made of the internally fogged silver halide emulsion, and the auxiliary layer contains substantially non-light-sensitive silver halide grains having an average grain size of not more than 0.5μm and is provided outside of and on the same side of the support as a light sensitive emulsion layer which is the outermost light-sensitive emulsion layer from the support, and wherein the amount of the substantially non-light-sensitive silver halide grains coated is from $1\times10^{-4}$ to $1\times10^{-2}$ mol/m$^2$ and wherein said silver halide photographic material contains no metallic salts coated with a less solubilizing agent, wherein said photographic material comprises a support, an emulsion layer containing a light-sensitive silver halide containing silver iodide and an internally fogged silver halide, provided on the support, and an auxiliary layer provided on the emulsion layer.

11. A silver halide photographic material as in claim 10, wherein an emulsion layer containing a light-sensitive silver halide is further provided between the emulsion layer and the auxiliary layer.

12. A silver halide photographic material as in claim 1, wherein said photographic material comprises a support, an emulsion layer containing an internally fogged silver halide provided on the support, an emulsion layer containing a light-sensitive silver halide containing silver iodide provided on the above emulsion layer, and an auxiliary layer provided on the latter emulsion layer.

13. A silver halide photographic material as in claim 1, wherein the compound represented by formula (I) is used in an amount of from $1\times10^{-3}$ to 10 mols per mol of silver halide in the auxiliary layer.

14. A silver halide photographic material comprising a support bearing on at least one side thereof at least one silver halide photographic emulsion layer and at least one auxiliary layer, wherein the silver halide photographic emulsion layer is a layer made of a light-sensitive silver halide emulsion containing silver iodide and an internally fogged silver halide emulsion, or is composed of a layer made of the light-sensitive silver halide emulsion containing silver iodide and a layer made of the internally fogged silver halide emulsion, and the auxiliary layer contains substantially non-light-sensitive silver halide grains having an average grain size of not more than 0.5μm and is provided outside of and on the same side of the support as a light sensitive emulsion layer which is the outermost light-sensitive emulsion layer from the support, wherein the amount of the substantially non-light-sensitive silver halide grains coated is from $1\times10^{-4}$ to $1\times10^{-2}$ and wherein iodides released from the exposed light-sensitive particles during development cause development of the internally-fogged silver halide particles present in the same or adjacent layer.

* * * * *